Figure 1:
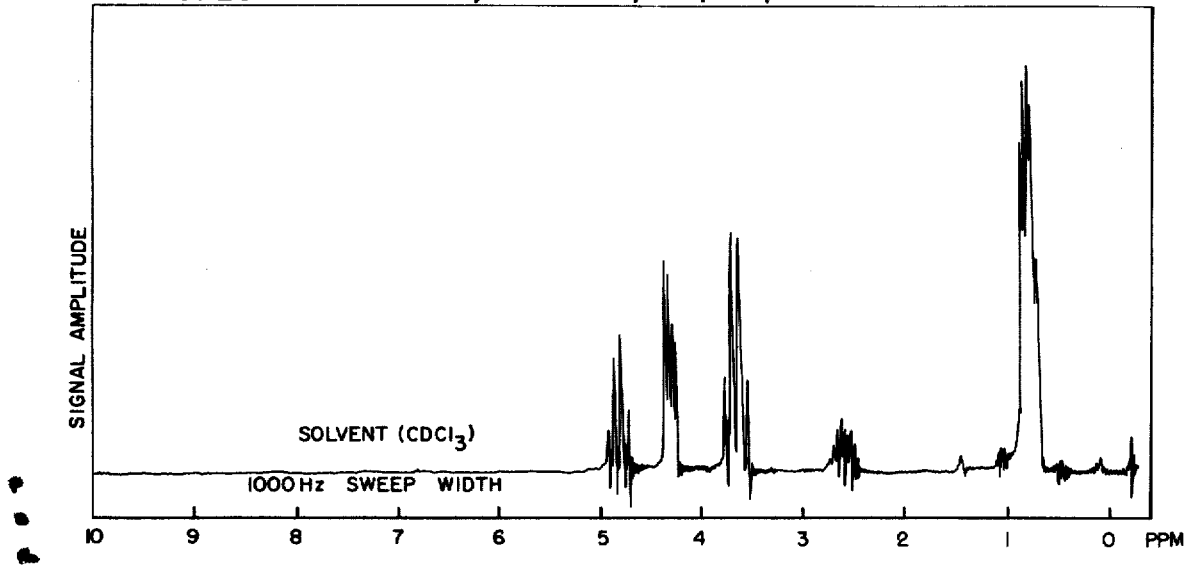

United States Patent [19]

Hall et al.

[11] 3,984,579

[45] Oct. 5, 1976

[54] NOVEL FLAVORING COMPOSITIONS AND PRODUCTS CONTAINING ISOMER MIXTURES CONTAINING HIGH PROPORTIONS OF 2-METHYL-CIS-3-PENTENOIC ACID

[75] Inventors: John B. Hall, Rumson; Manfred Hugo Vock, Locust; Joaquin Vinals, Red Bank, all of N.J.; Edward J. Shuster, Brooklyn, N.Y.

[73] Assignee: International Flavors & Fragrances Inc., New York, N.Y.

[22] Filed: May 9, 1975

[21] Appl. No.: 576,160

Related U.S. Application Data

[63] Continuation-in-part of Ser. No. 490,717, July 22, 1975, Pat. No. 3,931,306, which is a continuation-in-part of Ser. No. 408,854, Oct. 23, 1973, abandoned.

[52] U.S. Cl. .............................. 426/534; 424/365; 426/536; 426/537; 426/538
[51] Int. Cl.² ................. A23L 1/226; A23L 1/235; A61K 47/00
[58] Field of Search ............ 424/314, 365; 426/534, 426/536, 537, 538

[56] References Cited
OTHER PUBLICATIONS

Mussinan et al–J. Agric. Food Chem. vol. 23 No. 3 (1975) pp. 482–484.

Kratz et al–Chem. Abst. vol. 72 (1970) p. 53920t.

*Primary Examiner*—Sam Rosen
*Attorney, Agent, or Firm*—Arthur L. Liberman; Harold Haidt

[57] ABSTRACT

Methods are described for producing mixtures containing greater than 50% 2-methyl-cis-3-pentenoic acid as well as substantially pure 2-methyl-cis-3-pentenoic acid for preparing foodstuffs, flavoring compositions for foodstuffs, chewing gum compositions, flavoring compositions for chewing gum, medicinal product compositions and ingredients for medicinal product compositions by including therein the isomeric mixtures containing greater than 50% cis-2-methyl-3-pentenoic acid produced by the above-stated processes in order to produce in foodstuff flavorings, medicinal product flavorings and chewing gum flavorings, a sweet, fruity, strawberry, winey-cognac, butter-like, rum-like and butterscotch aroma and a sweet, strawberry, nutty-coconut, fatty, butter-like, rum-like and butterscotch-like taste with fruity, coconut-like isovaleric undertones.

11 Claims, 5 Drawing Figures

EXAMPLE IX, FRACTION 10
NMR SPECTRUM for Ethyl-2-methyl-3,4-pentadienoate

EXAMPLE IX, FRACTION 10

INFRA RED SPECTRUM for Ethyl-2-methyl-3,4-pentadienoate

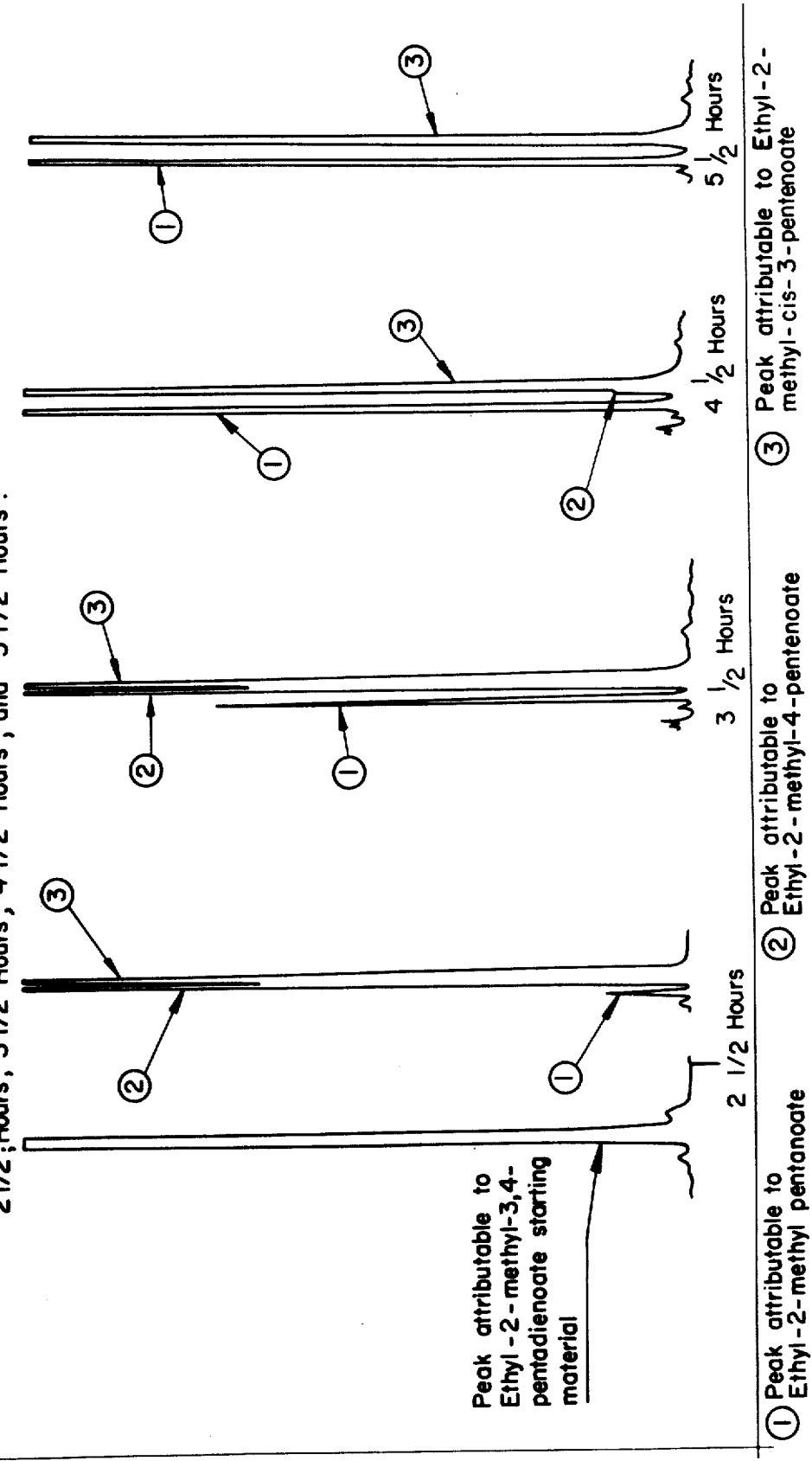

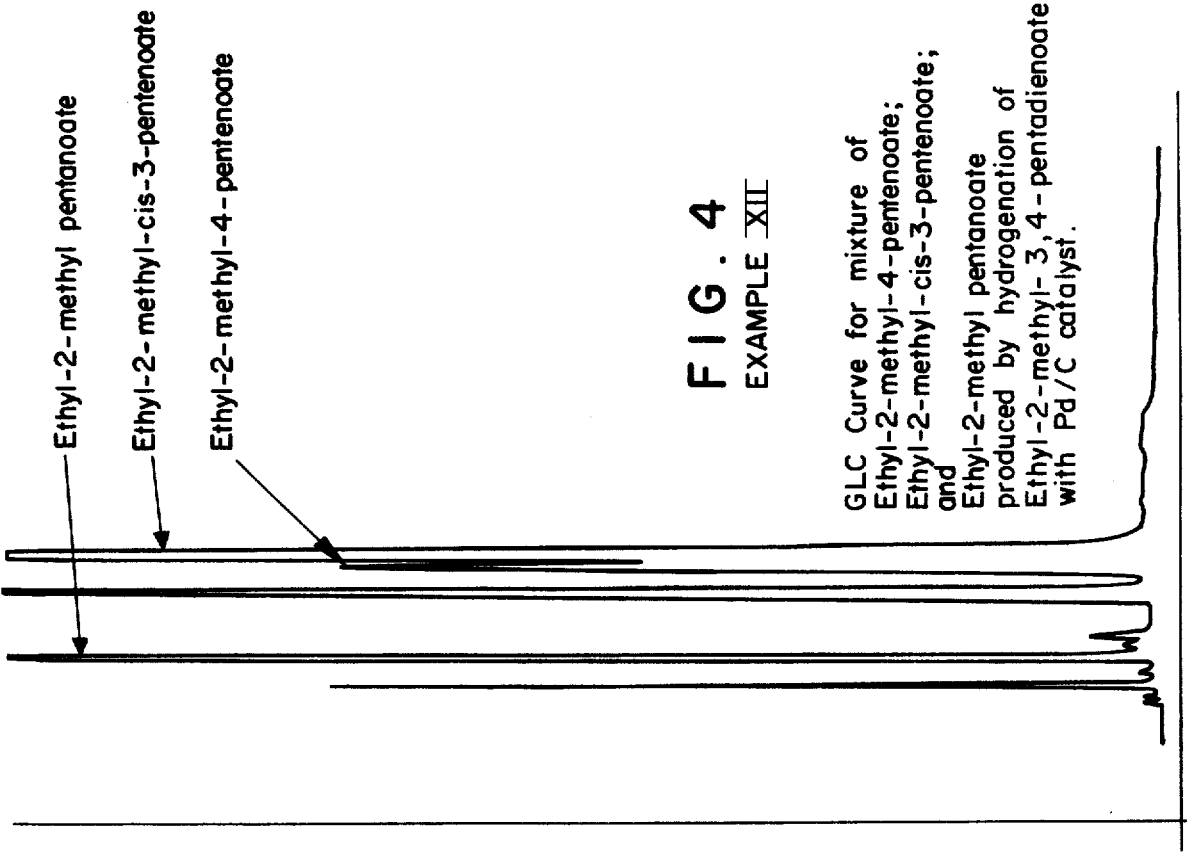

FIG. 4
EXAMPLE XII

GLC Curve for mixture of Ethyl-2-methyl-4-pentenoate; Ethyl-2-methyl-cis-3-pentenoate; and Ethyl-2-methyl pentanoate produced by hydrogenation of Ethyl-2-methyl-3,4-pentadienoate with Pd/C catalyst.

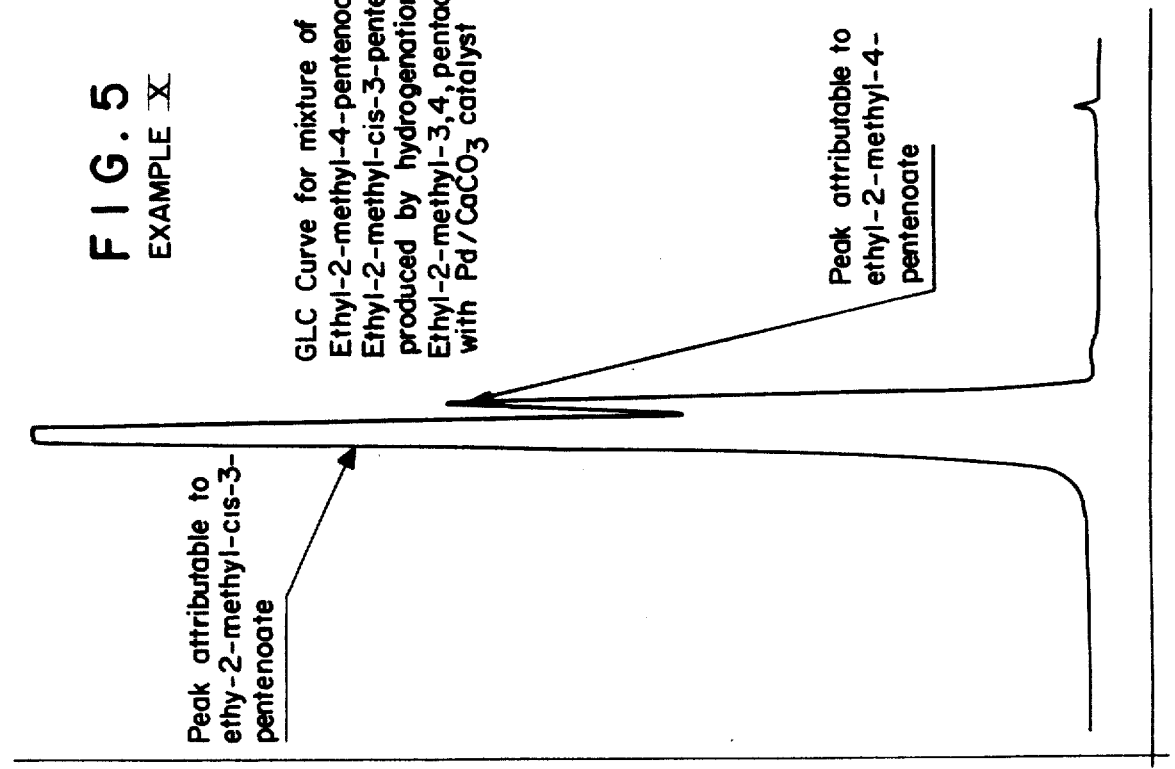

FIG. 5
EXAMPLE X

GLC Curve for mixture of Ethyl-2-methyl-4-pentenoate and Ethyl-2-methyl-cis-3-pentenoate produced by hydrogenation of Ethyl-2-methyl-3,4,pentadienoate with Pd/CaCO₃ catalyst

NOVEL FLAVORING COMPOSITIONS AND PRODUCTS CONTAINING ISOMER MIXTURES CONTAINING HIGH PROPORTIONS OF 2-METHYL-CIS-3-PENTENOIC ACID

This application is a continuation-in-part of U.S. application Ser. No. 490,717 filed on July 22, 1975, now U.S. Pat. No. 3,931,306 which is, in turn, a continuation-in-part of U.S. application Ser. No. 408,854 filed on Oct. 23, 1973 and now abandoned.

BACKGROUND OF THE INVENTION

The present invention relates to isomeric mixtures containing greater than 50% cis-2-methyl-3-pentenoic acid produced by, interalia, a number of processes and novel compositions using such mixtures of cis and trans isomers of 2-methyl-3-pentenoic acid to alter the flavor of foodstuffs, chewing gum and medicinal products.

There has been considerable work performed related to substances which can be used to impart (or enhance) flavors to (or in) various consumable materials, e.g., foodstuffs, medicinal products and chewing gums. These substances are used to diminish the use of natural materials, some of which may be in short supply and to provide more uniform properties in the finished product. Sweet, fruity, strawberry, winey-cognac, butter-like, rum-like, and butterscotch aromas as well as sweet, strawberry, nutty-coconut, fatty, butter-like, rum-like and butterscotch-like tastes are particularly desirable for many uses in foodstuff flavors, medicinal product flavors and chewing gum flavors.

U.S. Pat. No. 3,499,769 issued on Mar. 10, 1970 discloses processes for imparting a fresh fruity flavor (particularly strawberry flavor) to foods by adding a small amount of 2-methyl-2-pentenoic acid to the foodstuff. In U.S. Pat. No. 3,499,769 it is emphasized that the basic nuance imparted by 2-methyl-2-pentenoic acid is a "berry" flavor. Quite unexpectedly, the novel isomeric mixtures of the instant invention have properties different in kind from the 2-methyl-2-pentenoic acid of U.S. Pat. No. 3,499,769 which is only fruity and strawberry-like and does not have the sweet, fruity, butter-like, rum-like, and butterscotch aroma and taste qualities of the isomeric mixtures of the instant invention.

Other isomeric mixtures of 2-methyl-3-pentenoic acid are shown to be prepared by Boorman and Linstead, J. Chem. Soc. 1935, 258–67 (abstracted by Chem. Abstracts, Vol. 29, pages 2912 (7/8). 2-Ethyl-3-pentenoic acid is shown to be prepared by Fichter and Obladen, Berichte, 42, 4703-7 by distillation of alpha-ethyl gamma methyl paraconic acid which, in turn, is formed by reduction using a sodium-mercury amalgam of ethyl-alpha-ethyl aceto-succinate. The above-disclosed processes produce isomer mixtures which are considered to be different in kind insofar as their organoleptic properties are concerned from the isomer mixtures produced by the process of the instant invention.

Ethyl-2-methyl-3-pentenoate (95% 3:1 trans:cis isomer and 5% ethyl-2-methyl-2-pentenoate) has been offered as a development chemical by Toray Industries, Inc. of 2, Nihonbashi-Muromachi 2-chome, Chuo-Ku, Tokyo, Japan.

McGreer, et al, Can. J. Chem. 41, 726–31 (1963) discloses the production of various alkyl esters of pentenoic and butenoic acids by means of pyrolysis of 3,5-dimethyl-3-carbomethoxy $^1$-pyrazoline. Thus, on page 728 of the McGreer article, products having the following structures are shown to be produced:

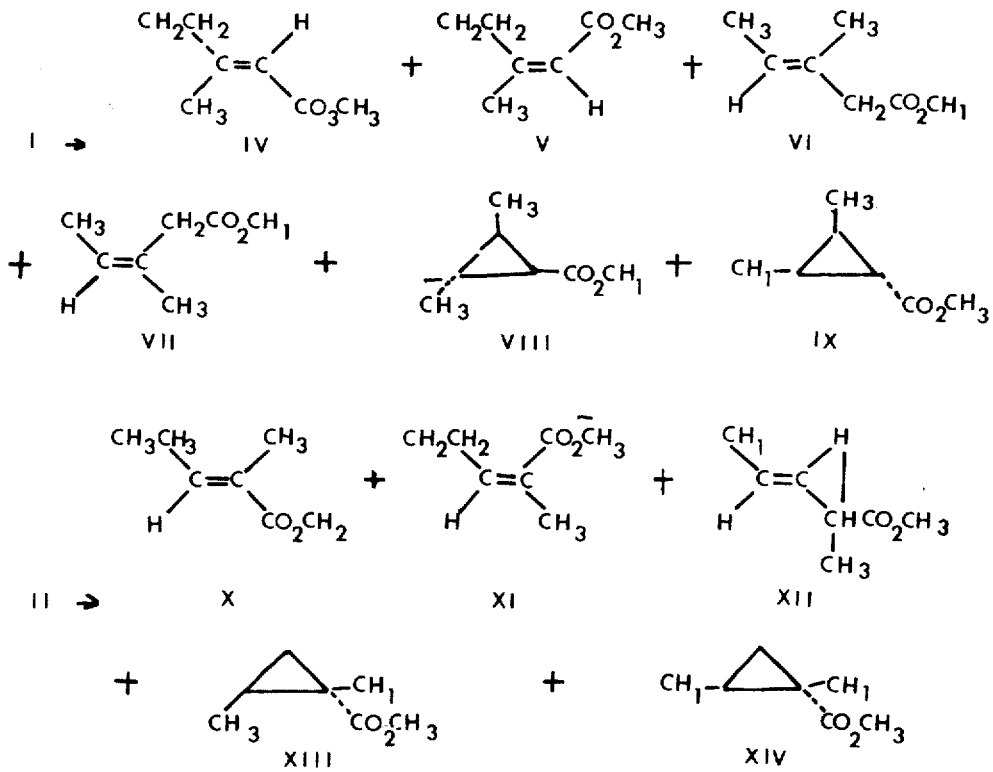

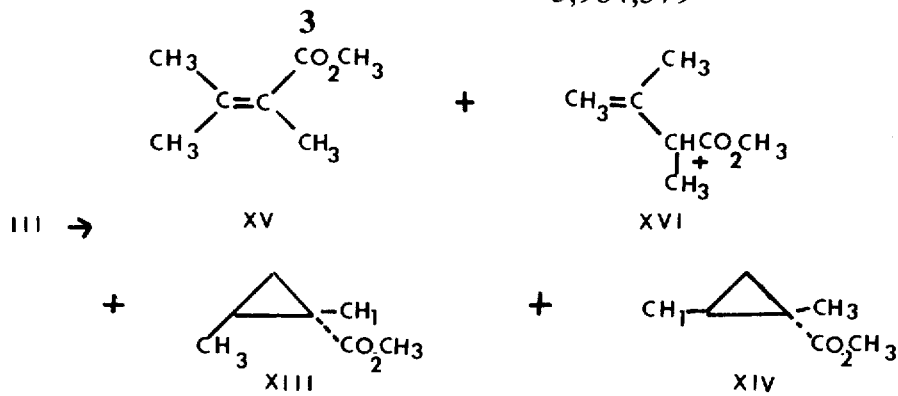

Tsuji, et al, J. Am. Chem. Soc., 86, (20) 4350-3 (1964) discloses the production of alkyl alkenoates by means of reaction of carbon monoxide, alkenyl halides and alkanols with use of palladium chloride as a catalyst. Other methods for the synthesis of alkyl alkenoates are set forth in the following references:

i. French Patent No. 1,398,856, issued February 19, 1965;

ii. Brewis and Hughes, Chem. Communications, (8), 157-8 (1965);

iii. Bordenca and Marsico, Tetrahedron Letters (16), 1541-3 (1967); and iv. Hosaka and Tsuji, Tetrahedron, 27, (16) 3821-9 (1971).

None of the above references sets forth a process for preparing the cis isomer of an alkyl pentenoic acid or mixtures containing more than 50% cis isomer.

Felkin, et al, Ann. Chem. (Paris) 6 (1), 17-26 (1971) discloses processes for producing high cis and high trans 2-methyl-3-pentenoic acid and methyl-2-methyl-3-pentenoate mixtures, according to the following reaction sequences:

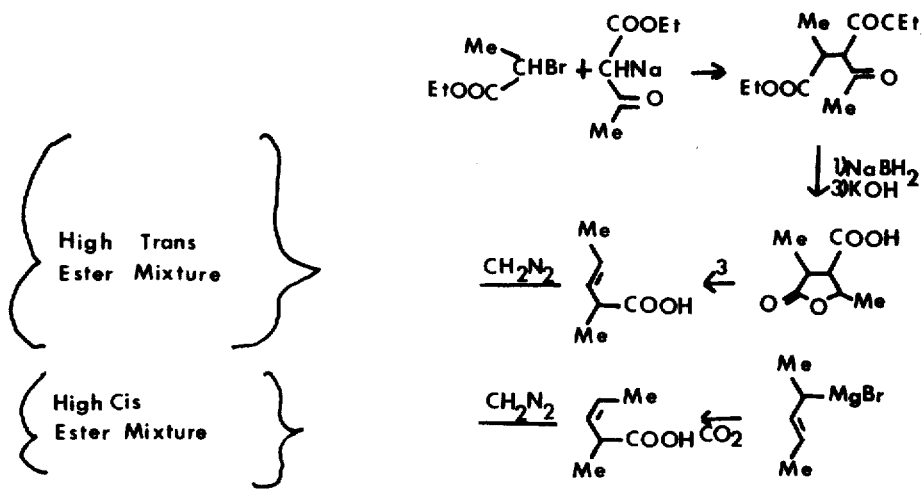

A process for preparing the high cis acid mixture is set forth in Felkin, et al, Chemical Communications, No. 802, pages 75 and 76 (Dec. 29, 1965).

THE INVENTION

It has now been discovered that solid and liquid foodstuffs, chewing gums and medicinal products and flavoring compositions therefor having sweet, fruity, strawberry, winey-cognac, butter-like, rum-like, butterscotch-like aromas and sweet, strawberry, nutty-coconut, fatty, butter-like, rum-like and butterscotch-like, taste notes may be provided by the utilization of isomer mixtures containing more than 50% cis-2-methyl-3-pentenoic acid (hereinafter termed "high cis-2-methyl-3-pentenoic acid" produced either (i) according to a process involving the steps of first preparing a 2-halo-3-pentene; then admixing said 2-halo-3-pentene with magnesium to form a 2-magnesium halo-3-pentene; then reacting said 2-magnesium halo-3-pentene with carbon dioxide to form a magnesium halo salt of 2-methyl-3-pentenoic acid and finally hydrolyzing the said salt in the presence of acid to form a novel isomer mixture containing a ratio of 60% cis-2-methyl-3-pentenoic acid and 40% trans-2-methyl-3-pentenoic acid; or (ii) according to a process involving first reacting methyl acetylene with a methyl magnesium halide to form a methylacetylene magnesium halide Grignard reagent; then reacting the methyl acetylene magnesium halide Grignard reagent with acetaldehyde to form a 3-pentyn-2-ol magnesium halide salt; then hydrolyzing the magnesium halide salt to form 3-pentyne-2-ol; then halogenating the 3-pentyne-2-ol to form a 4-halo-2-pentyne; then reacting magnesium with the 4-halo-2-pentyne to produce a 4-magnesium halo-2-pentyne Grignard reagent; then reacting the 4-magnesium-halo-2-pentyne Grignard reagent with carbon dioxide to form a magnesium halo-carboxylate salt mixture of compounds having the structures:

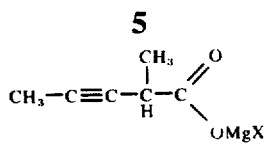

and

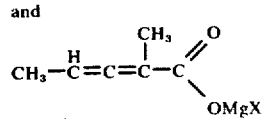

(wherein X is halogen); then hydrolyzing the magnesium halo-carboxylate salt mixture to form a mixture of carboxylic acids having the structures:

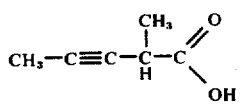

and

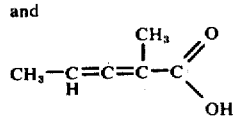

then hydrogenating the aforementioned mixture of carboxylic acids to form a mixture containing 80% cis-2-methyl-3-pentenoic acid and 20% 2-methyl-2-pentenoic acid; or (iii) according to a process comprising the steps of first reacting a 1,1,1-trilower alkoxy propane with 2-propynol-1 to form an alkyl-2-methyl-3,4-pentadienoate; then, in the alternative, either (i) hydrogenating with hydrogen gas the thus-formed alkyl-2-methyl-3,4-pentadienoate in the presence of a Raney nickel catalyst or a Palladium-on-carbon catalyst or a Palladium-on-calcium carbonate catalyst thereby forming a mixture containing at least 60% of alkyl-2-methyl-cis-3-pentenoate and, in addition, at most 40% of alkyl-2-methyl-4-pentenoate and/or alkyl-2-methyl pentenoate such as the ethyl, isobutyl or hexyl ester thereof; (ii) optionally, fractionally distilling the resulting mixture of esters so produced in order to increase the percentage of alkyl-2-methyl-cis-3-pentenoate, therein (up to 100% alkyl-2-methyl-cis-3-pentenoate) and (iii) saponifying the 100% alkyl-2-methyl-cis-3-pentenoate or ester mixture containing same with base to form a alkali metal salt of 2-methyl-cis-3-pentenoic acid (and, in certain cases, 2-methyl-4-pentenoic acid and/or 2-methyl pentenoic acid) and then acidifying the alkali metal salt of 2-methyl-cis-3-pentenoic acid (singly or in admixture with the alkali metal salts of the other carboxylic acids) with strong acid to form the 2-methyl-cis-3-pentenoic acid itself (singly or in admixture with the other named carboxylic acids); (iv) optionally, in the event that the thus-produced 2-methyl-cis-3-pentenoic acid is in admixture with 2-methyl-4-pentenoic acid and/or 2-methyl pentenoic acid, it may be desired, for purposes of achieving the specific taste and aroma characteristics of the 2-methyl-cis-3-pentenoic acid, to fractionally distill the mixture whereby mixtures containing high percentages (e.g., 80 or 90 or 95%) of 2-methyl-cis-3-pentenoic acid or 100% 2-methyl-cis-3-pentenoic acid are produced.

The "high cis" 2-methyl-3-pentenoic acid of our invention is intended to include singly and in admixture the two stereoisomers of 2-methyl-3-pentenoic acid having the structures:

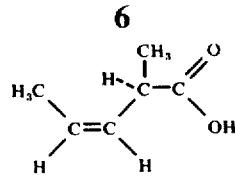

and

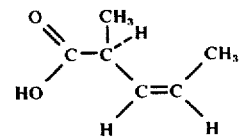

Thus, the high cis 2-methyl-3-pentenoic acid of our invention is capable of supplying and/or potentiating certain flavor notes usually lacking in many fruit flavors for use in foodstuffs, chewing gums and medicinal products not heretofore provided.

One process, set forth in the prior art, for producing a high cis-2-methyl-3-pentenoic acid isomer mixture involves the steps of:

a. First preparing a 2-halo-3-pentene by intimately admixing hydrogen bromide with 1,3-pentadiene at a temperature of from −20°C up to +30°C, preferably, from 0° up to 10°C and at a pressure, preferably, of atmospheric pressure. The 1,3-pentadiene (otherwise known as piperylene preferably has a purity of 90% but 50% piperylene may also be used. The 2-halo-3-pentene thus produced may be used in its crude form without further purification in subsequent reactions;

b. The 2-halo-3-pentene is then reacted with magnesium to form a Grignard reagent, otherwise known as 2-magnesium halo-3-pentene. The reaction with the magnesium is carried out preferably in the presence of tetrahydrofuran, however, other solvents such as diethyl ether may also be used. The mole ratio of magnesium to halo-pentene is preferably from 1 up to 10 moles of magnesium per mole of halo-pentene. More preferably, from 3 up to 5 moles of magnesium per mole of halo-pentene. The temperature of reaction is from 10° up to 50°C; preferably from 10° up to 20°C. Temperatures lower than 10°C gives rise to a reaction rate which is too slow to be economical. Temperatures higher than 50°C give rise to side reactions causing an undue lowering of yield of product;

c. The Grignard reagent produced in step (b) is then reacted with carbon dioxide (preferably in the form of crushed dry ice). The reaction with carbon dioxide may also be carried out by bubbling carbon dioxide into the Grignard reagent at atmospheric pressure at a temperature of between −20°C up to +40°C, preferably from 0°C to 20°C or reacting the Grignard reagent with gaseous carbon dioxide at higher pressures of from 10 up to 100 pounds per square inch absolute at temperatures up to 50°C. When the reaction takes place with crushed dry ice, the temperature is the temperature of crushed dry ice. The carbonation forms magnesium halo salt of 2-methyl-3-pentenoic acid having the structure:

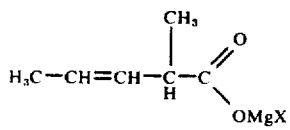

wherein X is halogen selected from the group consisting of chlorine and bromine;

d. The last step in this process of the prior art involves the hydrolysis of the magnesium halo salt of 2-methyl-3-pentenoic acid in acid at a pH of from 2 up to 3. The preferred acid is a mineral acid such as hydrochloric acid or sulfuric acid. A second process (which is novel) for producing another of the isomer mixtures containing a high proportion of cis-2-methyl-3-pentenoic acid, to wit approximately 80% cis-2-methyl-3-pentenoic acid and 20% 2-methyl-2-pentenoic acid involves the steps of:

a. First preparing a methyl acetylene magnesium halide Grignard reagent by admixing, a methyl magnesium halide (the chloride, bromide or iodide) with a slight molar excess of methyl acetylene (preferably as Mapp Gas, a commercial mixture of methyl acetylene and allene) at a temperature in the range of 40°–60°C (preferably 40°–50°C) in an inert solvent such as tetrahydrofuran or diethyl ether. Preferably, the reaction time range is from 4–12 hours;

b. Preparing 3-pentyne-2-ol by first admixing the methyl magnesium halide reaction product preferably in its original reaction solvent with a slight molar excess of acetaldehyde to form a magnesium halo salt of 3-pentyne-2-ol, at a temperature in the range of 20°C–30°C and then hydrolyzing the said magnesium halo salt of 3-pentyne-2-ol, preferably with a cold concentrated mineral acid such as concentrated hydrochloric acid in ice, and purifying the resulting 3-pentyne-2-ol using standard physical separation techniques, e.g., extraction and distillation;

c. Preparing a 4-halo-2-pentyne (e.g., 4-chloro-2-pentyne or 4-bromo-2-pentyne) by means of halogenating the 3-pentyne-2-ol with a slight molar excess halogenating agent, e.g., phosphorus trichloride, phosphorous tribromide, and $SOCl_2$, at temperatures in the range of 20°–80°C, depending upon the halogenation reagent used. The preferred halogenating reagent is $PCl_3$ using a temperature range of 20°–25°C;

d. Preparing a 4-magnesium-halo-2-pentyne Grignard reagent by reaction of the 4-halo-2-pentyne with magnesium in a solvent, for example, tetrahydrofuran or diethyl ether at a temperature in the range of 25°–50°C, depending upon the solvent used;

e. Preparing a magnesium halo carboxylate salt mixture of compounds having the structures:

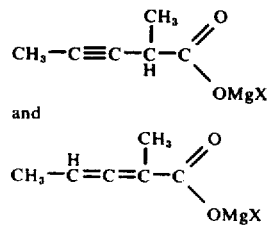

and (wherein X is halogen, e.g., chloro or bromo) by intimately admixing carbon dioxide (either in the gas phase, or as a solid in the form of powdered dry ice). The reaction with carbon dioxide may be carried out by bubbling carbon dioxide into the Grignard reagent at atmospheric pressure at a temperature of between −20°C up to +40°C, preferably, from 0°C to 20°C or reacting the Grignard reagent with gaseous carbon dioxide at higher pressures of from 10 up to 1000 pounds per square inch absolute at temperatures up to 50°C. When the reaction takes place with crushed dry ice, the temperature is the temperature of crushed dry ice;

f. Hydrolyzing the resulting magnesium halocarboxylate salt mixture with aqueous mineral acid (e.g., hydrochloric acid) at a temperature in the range of 20°–30°C to produce a crude mixture of:
 i. 2-methyl-3-pentynoic acid; and
 ii. 2-methyl-2,3-pentadienoic acid in a (i):(ii) ratio of 3:1;

g. Preparing a mixture containing about 80% cis-2-methyl-3-pentenoic acid and 20% 2-methyl-2-pentenoic acid by hydrogenating the mixed acid product of step (f) supra in the presence of a palladium/$CaSO_4$ catalyst containing 3% Pd preferably at a pressure in the range of 20–200 psig; preferably in a lower alkanol solvent such as methanol or ethanol at temperatures in the range of 20°C–40°C, preferably 20°C–25°C. The preferred weight percent range of catalyst is from 0.1 up to 1%. The resulting acid reaction product may then be purified using standard physical separation techniques, e.g., extraction and distillation.

A third process for producing the high cis 2-methyl-3-pentenoic acid including 100% 2-methyl-cis-3-pentenoic acid of our invention involves the steps of:

a. First reacting 1,1,1-trialkoxy propane (such as 1,1,1-triethoxy propane, or 1,1,1-trihexyloxy propane) with 2-propynol-1 in the presence of a propionic acid catalyst thereby providing the alkyl-2-methyl-3,4-pentadienoate starting material. The reaction temperature range is 120°–180°C with a range of 145°–150°C being preferred. The mole ratios of reactants preferred is 1:1 with a slight excess of either reactant being permissible. A large excess of 2-propynol-1 is undesirable, and a large excess of the trialkoxy propane is uneconomical. The percentage of propionic acid catalyst may vary from 1 up to 3%, but a 2% concentration of catalyst is preferred. Since the reaction temperature is in the range of 120°–180°C, higher pressures of reaction are required for the carrying out of the reaction; and, accordingly, pressures of from 30 up to 100 psig are used. The reaction time is inversely dependent on the temperature of reaction. Thus, for example, where the temperature range of reaction is 150°–160°C, the reaction time is approximately 3 hours. The length of reaction time varies between 2 and 6 hours, and a reaction time of 3–4 hours is preferred. The reaction product, the alkyl-2-methyl-3,4-pentadienoate, is then worked-up and this work-up operation is performed by first, if necessary, washing out the excess tri-alkyl orthopropionate reactant by washing with 5% hydrochloric acid solution. The acid is then neutralized by use of a sodium bicarbonate wash, and the reaction mass is then fractionally distilled.

b. The resulting alkyl-2-methyl-3,4-pentadienoate starting is then reacted with hydrogen in the presence of a Raney nickel catalyst or a palladium-on-carbon catalyst, or a Lindlar catalyst (palladium-on-calcium carbonate). The percentage of palladium in the palladium on carbon catalyst or in the palladium on calcium carbonate catalyst varies from about 1% up to about 7% with a percentage of palladium in the palladium-on-carbon catalyst or in the palladium on calcium carbonate catalyst being preferred to be 3–5%. The temperature of reaction for this hydrogenation may vary from about 10°C up to about 100°C with a preferred reaction temperature of 25°–35°C. Since the reaction is exothermic, it is usually necessary to provide external cooling to the reaction mass during the course of the reaction. The pressure of hydrogen over the reaction mass may vary from about 5 psig up to about 80 psig, with the most preferred pressure being 20 psig. It has been found that pressures above 20 psig give rise to a larger amount of undesired side products. The hydrogenation reaction may be carried out in the presence of or in the absence of a solvent. When a solvent is used, it is required that it be an inert (non-reactive solvent such as isopropyl alcohol, hexane or ethanol, with the alkyl moiety of the alcohol solvent being the same as the alkyl moiety of the alkoxy group of the ester being hydrogenated. If a solvent is used, it is preferred that the mole ratio of solvent:hydrogenated ester be approximately 1:1. Where a palladium-containing catalyst is used, the percentage of catalyst in the reaction mass may vary from 0.125 up to about 2.0% with a percentage of catalyst of about 0.25% being preferred. Where a Raney nickel catalyst is used, the percentage of catalyst in the reaction mass may vary from about 3 up to about 10% with a percentage of catalyst of about 5% being preferred. The hydrogenation reaction produces mixtures including alkyl-2-methyl-cis-3-pentenoate, alkyl-2-methyl-4-pentenoate and alkyl-2-methylpentenoate, all mixtures containing at least 60% alkyl-2-methyl-cis-3-pentenoate. As a result, the alkyl-2-methyl-cis-3-pentenoate of our invention may, if desired be separated and refined by means of fractional distillation. Where the catalyst used is a Lindlar catalyst (Palladium on calcium carbonate) a mixture of alkyl-2-methyl-cis-3-pentenoate and alkyl-2-methyl-4-pentenoate is produced. Where the catalyst used is palladium on carbon rather than palladium on calcium carbonate, a mixture of alkyl-2-methyl-cis-3-pentenoate, alkyl-2-methyl-4-pentenoate and alkyl-2-methyl pentenoate is formed. Where the catalyst used is Raney nickel rather than palladium on calcium carbonate, initially produced is a mixture of alkyl-2-methyl-cis-3-pentenoate, alkyl-2-methyl-4-pentenoate and alkyl-2-methyl pentenoate with the percentage of alkyl-2-methyl-cis-3-pentenoate being greater than 50% by weight of the total reaction product produced. As the hydrogenation proceeds, however, the percentage of alkyl-2-methyl-4-pentenoate diminishes to 0 and the percentage of alkyl-2-methyl pentenoate increases, with the quantity of alkyl-2-methyl-cis-3-pentenoate remaining the same. At the end of the hydrogenation reaction, the reaction mass is filtered in order to separate catalyst from liquid phase desired product, and the filtrate is distilled using a fractional distillation column operated under vacuum.

c. The resulting alkyl-2-methyl-cis-3-pentenoate (and, as the case may be, other esters which may not have been separated therefrom after the hydrogenation reaction) are converted into the corresponding carboxylic acids by the standard saponification and acidification reactions. The saponification is preferably carried out using strong aqueous base, e.g., 50% aqueous sodium hydroxide or 50% aqueous potassium hydroxide admixed with methanol. After acidification of the resulting salt of the carboxylic acid (e.g., the sodium or potassium salt) is acidified using mineral acid (e.g., a 6 molar aqueous hydrochloric acid), and the 2-methyl-cis-3-pentenoic acid is extracted from the aqueous phase using an organic solvent such as toluene. The organic solvent is then stripped from the acid, and the acid is fractionally distilled. The foregoing series of reactions may be illustrated as follows:

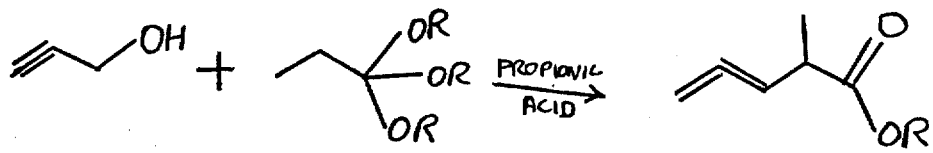

(b) 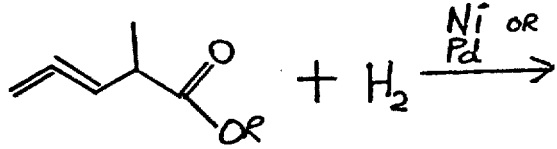

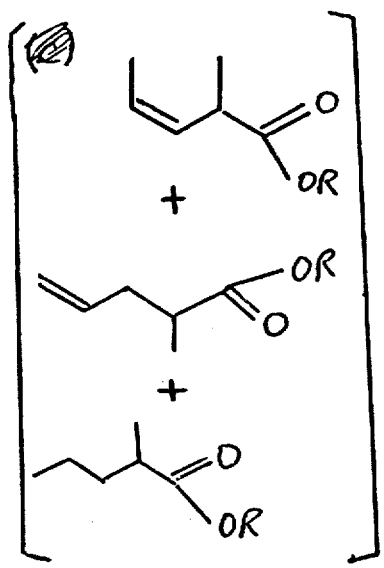

When the high cis 2-methyl-3-pentenoic acid isomer mixture or 2-methyl-cis-3-pentenoic acid per se of our invention is used as a food flavor adjuvant, or a chewing gum flavor adjuvant or a medicinal product flavor adjuvant, the nature of the co-ingredients included with the said high cis 2-methyl-3-pentenoic acid isomer mixture or 2-methyl-cis-3-pentenoic acid per se in formulating the product composition will also serve to alter the organoleptic characteristics of the ultimate foodstuff or chewing gum or medicinal product treated therewith.

As used herein, in regard to flavors the term alter in its various forms means "supplying or imparting flavor character or note to otherwise bland, relatively tasteless substances or augmenting the existing flavor characteristic where a natural flavor is deficient in some regard or supplementing the existing flavor impression to modify its quality, character or taste".

As used herein, the term "foodstuff" includes both solids and liquids ingestible materials which usually do, but need not, have nutritional value. Thus, foodstuffs include soups, convenience foods, beverages, dairy products, candies, vegetables, cereals, soft drinks, snacks and the like.

As used herein, the term medicinal product includes both solids and liquids which are ingestible materials which have medicinal value such as cough syrups, cough drops, laxitives, aspirin, chewable medicinal tablets containing antibiotics and sore throat lozenges.

The term chewing gum is herein intended to be definitive of a composition which comprises a substantially water-insoluble, chewable, plastic gum base such as chicle, or substitutes therefor, including jelutong, qut-takay rubber or certain comestible natural or synthetic resins or waxes. Incorporated with the gum base, and in admixture therewith, may be plasticizers or softening agents, e.g., glycerine; and a flavoring composition with incorporates the high cis 2-methyl-3-pentenoic acid mixture or 2-methyl-3-pentenoic acid per se of our invention, and in addition sweetening agents which may be sugars including sucrose or dextrose and/or artificial sweeteners such as cyclamates or saccharin. Other optional ingredients may also be present.

Substances suitable for use herein as co-ingredients or flavoring adjuvants are well known in the art for such use being extensively described in the relevant literature. Apart from the requirement that any such material be "ingestibly" acceptable and thus non-toxic or otherwise non-deleterious nothing particularly critical resides in selection thereof. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2 and 3 tertiary-butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agaragar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches pectins, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, beta, beta-dimethyl-acrolein, n-hexanal, 2-hexenal, cis-3-hexenal, 2-heptanal, 4-(p-hydroxyphenyl)-2-butanone, alpha-ionone, beta-ionone, methyl-3-butanone, 2-pentanone, 2-pentenal and propanal; alcohols, such as 1-butanal, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpineol, cis-terpineol hydrate; esters, such as butyl acetate, ethyl acetate, ethyl acetoacetate, ethyl benzoate, ethyl butyrate, ethyl caproate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl capronate, methyl isobutyrate, alphamethylbutyrate, propyl acetate, amyl acetate, amyl butyrate, benzyl salicylate, dimethyl anthranilate, ethyl methylphenylglycidate, ethyl succinate, isobutyl cinnamate and terpenyl acetate; essential oils, such as jasmine absolute, rose absolute, orris absolute, lemon essential oil, Bulgarian rose, yara yara, natural raspberry oil and vanilla; lactones; sulfides, e.g., methyl sulfide and other materials such as maltol, acetoin and acetals (e.g., 1,1-diethoxyethane, 1,1-dimethoxyethane and dimethoxymethane.

The specific flavoring adjuvant selected for use may be either solid or liquid depending upon the desired physical form of the ultimate product, i.e., foodstuff, medicinal product or chewing gum, whether simulated or natural, and should, in any event, be capable of providing an environment in which the high cis 2-methyl-3-pentenoic acid or 2-methyl-cis-3-pentenoic acid, per se, of our invention can be dispersed or admixed to provide a homogeneous medium. In addition, selection of one or more flavoring adjuvants, as well as the quantities thereof, will depend upon the precise organoleptic character desired in the finished product. Thus, in the case of flavoring compositions, ingredient selection will vary in accordance with the foodstuff or chewing gum or medicinal product to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of high cis 2-methyl-3-pentenoic acid mixture or 2-methyl-cis-3-pentenoic acid, per se, employed in a particular instance can vary over a relatively wide range whereby to its desired organoleptic effects having reference to the nature of the product are achieved. All parts and percentages given herein are by weight unless otherwise specified. Thus, correspondingly greater amounts would be necessary in those instances wherein the ultimate food composition or chewing gum composition or medicinal product composition to be flavored is relatively bland to the taste, whereas relatively minor quantities may suffice for purposes of enhancing the composition merely deficient in natural flavor or aroma. Thus, the primary requirement is that the amount selected to be effective, i.e., sufficient to alter the organoleptic characteristics of the parent composition, whether foodstuff per se, chewing gum per se, medicinal product per se or flavoring composition. Thus, the use of insufficient quantities of high cis 2-methyl-3-pentenoic acid mixture, or 2-methyl-cis-3-pentenoic acid of our invention will, of course, substantially vitiate any possibility of obtaining the desired results while excess quantities prove needlessly costly and in extreme cases, may disrupt the flavor-aroma balance, thus providing self-defeating. Accordingly, the terminology, effective amount and sufficient amount is to be accorded a significance in the context of the present invention consistent with the obtention of desired flavoring effects.

Thus, and with respect to ultimate food compositions, ultimate chewing gum compositions and ultimate medicinal product compositions, it is found that quantities of high cis 2-methyl-3-pentenoic acid or 2-methyl-cis-3-pentenoic acid ranging from a small but effective amount, e.g., 0.01 parts per million up to about 50 parts per million by weight based on total composition are suitable. Concentrations in excess of the maximum quantity stated are not normally recommended since they fail to prove commensurate enhancement of organoleptic properties. In those instances wherein the high cis 2-methyl-3-pentenoic acid mixture or 2-methyl-cis-3-pentenoic acid, per se is added to the foodstuff or chewing gum or medicinal product, as the case may be, as an integral component of a flavoring composition, it is, of course, essential that the total quantity of flavoring composition employed be sufficient to yield an effective high cis 2-methyl-3-pentenoic acid concentration or 2-methyl-cis-3-pentenoic acid concentration in the foodstuff product, medicinal product or chewing gum.

Medicinal product, chewing gum and food flavoring compositions prepared in accordance with the present invention preferably contain the high cis 2-methyl-3-pentenoic acid or 2-methyl-cis-3-pentenoic acid in concentrations ranging from about 0.015% up to about 10% by weight based on the total weight of said flavoring composition.

The compositions described herein can be prepared according to conventional techniques well known as typified by cake batters and fruit juices can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the high cis 2-methyl-3-pentenoic acid mixture or 2-methyl-cis-3-pentenoic acid, per se with, for example, gum arabic, gum tragacanth, carrageenan and the like, and thereafter spray-drying the resultant mixture whereby to obtain the particular solid product. Pre-prepared flavor mixes in powder form, e.g., a vanilla powder mix or a walnut flavored powder mix are obtained by mixing the dried solid components, e.g., starch, sugar and the like and a high cis 2-methyl-3-pentenoic acid mixture or 2-methyl-cis-3-pentenoic acid of our invention in a dry blender until the requisite degree of uniformity is achieved.

It is presently preferred to combine with the high cis 2-methyl-3-pentenoic acid isomer mixture or 2-methyl-cis-3-pentenoic acid, per se of our invention, the following adjuvants:
Geraniol
Ethyl methyl phenyl glycidate
Vanillin
Ethyl pelargonate
Isoamyl acetate
Ethyl butyrate
Naphthyl ethyl ether
Ethyl acetate
Isoamyl butyrate
2-Methyl-2-pentenoic acid
Elemecine (4-allyl-1,2,6-trimethoxy benzene)
Isoelemecine (4-propenyl-1,2,6-trimethoxy benzene)

The following examples are given to illustrate embodiments of the invention as it is presently preferred to practice it. The following examples are given to illustrate methods for preparing high cis 2-methyl-3-pentenoic acid isomer mixtures and the 2-methyl-cis-3-pentenoic acid per se useful in the practice of our invention. It will be understood that these examples are illustrative, and the invention is not to be considered as restricted thereto except as indicated in the appended claims.

EXAMPLE I

PREPARATION OF AN APPROXIMATELY 60:40 CIS:TRANS MIXTURE 2-METHYL-3-PENTENOIC ACID

A. PREPARATION OF 4-CHLORO-2-PENTENE

Into a three liter flask equipped with stirrer, thermometer, reflux condenser, subsurface addition tube and inlet and outlet bubblers and cooling bath, 1000 gms. (14.8 moles) of 97.7% pure piperylene is charged. The piperylene is cooled to 10°C and the reaction vessel is purged with dry nitrogen. While passing in hydrogen chloride, the reaction mass is stirred vigorously and the reaction mass temperature is maintained at 10°–15°C with external cooling. The hydrogen chloride is added over a period of 7 hours. The reaction mass is then purged with nitrogen at room temperature for a period of 10–20 minutes to remove any excess hydrogen chloride. The crude product may then be used further without purification for the preparation of the 2-methyl-3-pentenoic acid isomer mixture. The amount of crude product obtained is 1,435 gms.

B. PREPARATION OF 2-METHYL-3-PENTENOIC ACID ISOMER MIXTURE

Into a twelve liter reaction vessel equipped with stirrer, thermometer, reflux condenser, dropping funnel, two bubblers, heating mantle and cooling bath, thoroughly purged with nitrogen, the following materials are charged:

| | |
|---|---|
| Magnesium Turnings | 600 gms. |
| Tetrahydrofuran | 3 liters |

The magnesium-tetrahydrofuran mixture is heated to 50°C at which time 70 ml of a solution (produced by admixing 750 gms of 4-chloro-2-pentene produced in step (A) with 2 liters of tetrahydrofuran) is added to the magnesium-tetrahydrofuran mixture in the 12-liter reaction vessel with stirring. The reaction mass temperature increases indicating the initiation of a Grignard reaction. With stirring, the remainder of the 4-chloro-2-pentene-tetrahydrofuran solution is added over a period of 5 hours. During the first 30 minutes of the addition, the reaction mass is slowly cooled to 25°–30°C and after that time the reaction mass is maintained at 25°–30°C throughout the remainder of the addition. The reaction mass is then stirred for 1 hour at 25°–30°C.

7.2 Kilograms of finely crushed dry ice is added into a 22 liter reaction flask equipped with an air driven motor stirrer, addition tube and an inlet and outlet bubblers. The Grignard reagent produced in the 12 liter reaction vessel is siphoned onto the dry ice in the 22 liter flask thus leaving the excess magnesium turnings in the 12 liter flask. A nitrogen stream is used to prevent premature reaction of carbon dioxide at the inlet tube. The dry ice-Grignard reagent mixture is then stirred slowly until the excess carbon dioxide has evaporated. The time of stirring is 8 hours. 2.5 Liters of water is then added to dissolve the magnesium salt and tetrahydrofuran is recovered by distillation at atmospheric pressure to pot temperature of 80°C. 1.25 Liters of toluene is then added to the reaction mass followed by 750 ml of concentrated hydrochloric acid over a period of 30 minutes maintaining the temperature of the reaction mass between 30°–40°C. The reaction mass is then stirred for another 30 minutes without further heating or cooling. The organic layer is removed and the aqueous layer is extracted with 1.25 liters of toluene after which time the two organic layers are combined. The organic solution is then stripped of solvent and the crude 2-methyl-3-pentenoic acid is rushed over to a pot temperature of 180°C at 2 mm Hg. using a 2 liter still with a 2 inch splash column. The rushed over 2-methyl-3-pentenoic acid is then fractionated at 3 mm Hg. pressure and a vapor temperature of 62°–63°C on a 1½ inch × 18 inch Goodloe packed column after adding 40 gms. of Primol and 1 gm of Ionol. NMR, IR and Raman spectral analyses indicate that the material produced is a 60:40 cis: trans mixture of isomers of 2-methyl-3-pentenoic acid (weight: 38 gms.).

NMR Analysis (CDCl$_3$):

| Signal | Interpretation |
| --- | --- |
| 1.24 (d, 3H) | —CH—C$\underline{H}_3$ |
| 1.69 (d, 3H) | =CH—C$\underline{H}_3$ |
| (3.10)(3.50) (m, 1H) | —C$\underline{H}$— (Shows cis:trans ratio of 3:2) |
| 5.52 ppm (m, 2H) | —C$\underline{H}$=C$\underline{H}$— |

NOTE: (Signal at 3.50 ppm attributed to "cis" isomer, and 3.10 ppm attributed to "trans" isomer.

EXAMPLE II

The following concentrate is prepared:

| Ingredient | Percent |
| --- | --- |
| Geraniol | 1.00 |
| Ethyl methyl phenyl glycidate | 3.33 |
| High cis-2-methyl-3-pentenoic acid (prepared according to the process of Example I) | 4.77 |
| Vanillin | 5.66 |
| Ethyl pelargonate | 13.06 |
| Isoamyl acetate | 14.00 |
| Ethyl butyrate | 58.18 |

EXAMPLE III

Another concentrate is prepared as follows:

| Ingredient | percent |
| --- | --- |
| Naphthyl ethyl ether | 0.96 |
| Vanillin | 2.66 |
| Ethyl methyl phenyl glycidate | 2.88 |
| High cis-2-methyl-3-pentenoic acid (prepared according to the process of Example I) | 4.90 |
| Ethyl acetate | 9.58 |

-continued

| Ingredient | percent |
| --- | --- |
| Isoamyl acetate | 12.25 |
| Ethyl butyrate | 26.20 |
| Isoamyl butyrate | 40.57 |

EXAMPLE IV

The concentrate prepared in Example II is dissolved in 4 volumes of propylene glycol and the mixture is added to a hard candy melt at the rate of 1.5 oz of the concentrate solution per 100 lbs. of melt. After the finished candy has been produced, it is found to have an excellent strawberry flavor. When the candy is compared with candy made under the same conditions, but without the 2-methyl-3-pentenoic acid prepared according to the process of Example I in the concentrate, it is found to have an inferior strawberry flavor.

EXAMPLE V

The propylene glycol solution of the concentrate as prepared in Example IV is added to a simple syrup at the rate of ⅛ oz. per gallon of syrup. The syrup is acidified by the addition of 1.5 oz. of 50% aqueous citric acid solution to each gallon of syrup. A carbonated beverage is prepared by admixing one oz. of the flavored, acidified syrup with 5 oz. of carbonated water. The beverage so prepared has an excellent fresh strawberry flavor, and is found to be markedly superior to a beverage prepared in the same manner but without the high cis-2-methyl-3-pentenoic acid prepared according to the process of Example I.

EXAMPLE VI

The flavor concentrate prepared in Example III is admixed with gum arabic and in the proportion of 7 lbs. of concentrate to 28 lbs. of gum arabic in 65 lbs. of water, and the aqueous mixture is spray-dried. The flavor concentrate-carrier combination so obtained in then added to a gelatin dessert mix in the ratio of 1 oz. of spray-dried material to 100 lbs. of dessert mix powder. The gelatin dessert produced from the mix has an excellent strawberry flavor and is markedly superior to the gelatin dessert prepared in the same manner without the 2-methyl-3-pentenoic acid prepared according to the process of Example I in the concentrate.

EXAMPLE VII

PREPARATION OF MIXTURE CONTAINING 80% CIS-2-METHYL-3-PENTENOIC ACID AND 20% 2-METHYL-2-PENTENOIC ACID

A. PREPARATION OF 3-PENTYN-2-OL

| Equipment: | 5 liter reaction flask | |
| --- | --- | --- |
| Material: | Methyl magnesium chloride (3 molar in tetrahydrofuran) | 3 liters |
| | MAPP gas (Mixture of methyl acetylene and allene) | 600 g |
| | Acetaldehyde (6 molar) | 264 g |

Procedure: Mapp gas is passed through a sodium hydroxide drying tube into the methyl magnesium chloride solution at 40°–50°C. The operation takes 5 hours to completion. The mixture is heated to 50°C for an additional 2 hours before cooling. To the cold solution is added 264 g of acetaldehyde at 20°–30°C over 2 hours with cooling. The mixture is then stirred for one hour at 25°C and is then decomposed with 800 ml of concentrated hydrochloric acid and 5 kg of ice. The resulting lower layer is extracted with one liter of benzene. The combined organic liquids are washed with two 200 ml portions of 20% aqueous NaCl and distilled at atmospheric pressure to a pot temperature of 92°C and then rushed over under vacuum. The rushed over material is then topped at 45–50 mm Hg. pressure to a pot temperature of 72°C (weight of product: 92 grams). After the topping, this material is used to prepare 4-chloro-2-pentyne in part B, infra, without further purification.

| B. PREPARATION OF 4-CHLORO-2-PENTYNE | | |
|---|---|---|
| Equipment: | 250 ml reaction flask | |
| Material: | 3-Pentyn-2-ol | 84 g (Ex part A) |
| | Phosphorous trichloride | 69 g |

Procedure: The phosphorus trichloride is added at 20°–25°C with cooling to the 3-pentyn-2-ol prepared in part A, supra. The mixture is stirred for 12 hours at 20°–25°C and then heated to 72°C for 5 hours. IR analysis indicates that the reaction is complete. The material is then rushed over under vacuum to give 4-chloro-2-pentyne for the Grignard reaction exemplified in part C, infra. The yield is nearly quantitative.

| C. PREPARATION OF 2-METHYL-3-PENTYNOIC ACID | | |
|---|---|---|
| Equipment: | 1 liter reaction flask | |
| Material: | 4-Chloro-2-pentyne | 46 g |
| | Magnesium chips | 60 g |
| | Tetrahydrofuran (dry) | 500 ml |

Procedure: 4-Chloro-2-pentyne is dissolved in 200 ml of tetrahydrofuran and added over 4½ hours (after starting the reaction with iodine crystals) to the magnesium chips in 300 ml of tetrahydrofuran. The reaction temperature rises to 44°–50°C in the initiation period and is maintained at 28°–30°C with external cooling. The reaction mixture is allowed to stir for an additional hour after all of the 4-chloro-2-pentyne is added. The resulting Grignard reagent is poured onto 620 g of dry ice (powdered) with stirring. After the $CO_2$ evaporates, 300 ml of water is added and the solution is extracted with three 200 ml portions of toluene. The toluene extracts are discarded. The aqueous solution is cooled and acidified with 50 ml of concentrated hydrochloric acid; then extracted with two 200 ml portions of toluene. The toluene extract, after washing with three 50 ml portions of 20% NaCl solution is stripped of solvent and rushed over to give 22 g of crude acids. The crude product is then fractionated in a semi-micro still to give 6.2 g of an acid mixture which contains a 3:1 mixture of 2-methyl-3-pentynoic acid and 2-methyl-2,3-pentadienoic acid.

| D. HYDROGENATION REACTION | | |
|---|---|---|
| Equipment: | Parr Shaker | |
| Material: | Mixture of 2-methyl-3-pentynoic acid and 2-methyl-2,3-pentadienoic acid | 4 g |
| | Methanol (absolute) | 50 ml |

| D. HYDROGENATION REACTION | |
|---|---|
| 3 % Pd/CaSO₄ | 0.1 g |

Procedure: The 2-methyl-3-pentynoic acid and 2-methyl-2,3-pentadienoic acid mixture produced in part C, supra, is hydrogenated at room temperature in methanol in the presence of Pd/CaSO₄ catalyst at a hydrogen pressure of 44.5 psig. The reaction is complete in 5 minutes. After removal of the methanol, the residue oil is analyzed by GLC which shows one peak. However, NMR analysis shows two products confirmed to be cis-2-methyl-3-pentenoic acid and 2-methyl-2-pentenoic acid. (A 4:1 mixture).

EXAMPLE VIII

FLAVOR FORMULATION CONTAINING MIXTURE OF 80% 2-METHYL-CIS-3-PENTENOIC ACID AND 20% 2-METHYL-2-PENTENOIC ACID

The following basic strawberry formulation is prepared:

| Ingredient | Parts by Weight |
|---|---|
| Parahydroxy benzyl acetone | 0.2 |
| Vanillin | 1.5 |
| Maltol | 2.0 |
| Ethyl-3-methyl-3-phenyl glycidate | 1.5 |
| Benzyl acetate | 2.0 |
| Ethyl butyrate | 1.0 |
| Methyl cinnamate | 0.5 |
| Methyl anthranilate | 0.5 |
| Alpha-ionone | 0.0 |
| Gamma undecalactone | 0.2 |
| Diacetyl | 0.2 |
| Anethole | 0.1 |
| Cis-3-hexenol | 1.7 |
| 95% aqueous ethanol | 38.5 |
| Propylene glycol | 50.0 |
| | 100.0 |

To a portion of the foregoing formulation, 0.2% by weight of a mixture of 80% cis-2-methyl-3-pentenoic acid and 20% 2-methyl-2-pentenoic acid prepared according to the process of Example VII is added. The formulation with the high cis 2-methyl-3-pentenoic acid is compared to the same formulation without said high cis 2-methyl-3-pentenoic acid.

Both flavors are evaluated in a milk beverage sweetened with 10% sugar at the rate of 100 ppm. Both beverages are tasted by an expert panel. The beverage containing the strawberry formulation with the addition of the mixture containing 80% 2-methyl-cis-3-pentenoic acid is unanimously preferred as having a more natural like, strawberry aroma, a sweeter, more green, more pleasant strawberry taste and a sweet, strawberry after-taste.

EXAMPLE IX

PREPARATION OF ETHYL-2-METHYL-3,4-PENTADIENOATE

Reaction:

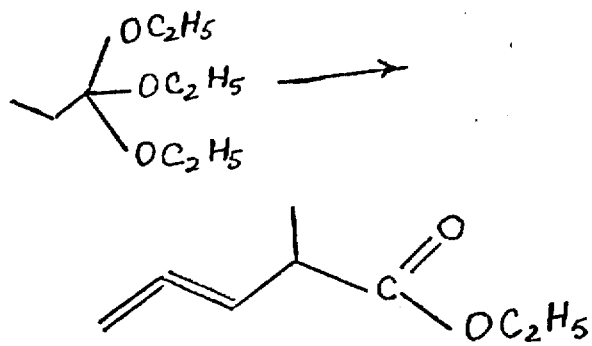

Into a 2 liter autoclave, the following materials are placed:

| Ingredient | Amount |
|---|---|
| Triethyl orthopropionate | 495 grams |
| 2-Propyn-1-ol | 90 grams |
| Propionic acid | 12 grams |

The autoclave is closed and the reaction mass is heated to 150°C. over a period of 50 minutes. The reaction mass is then maintained at a temperature of between 135°–160°C and at a pressure of 20 up to 60 psig for a period of 3 hours. At the end of this 3-hour period, the autoclave is opened and the reaction mass is cooled to room temperature. 12.6 g of sodium bicarbonate is then added to the reaction mass in order to neutralize the propionic acid. 30 g of Primol (see note 1) and 0.1 g of Ionol[R] (see note 2) are added and the resulting reaction product is fractionally distilled at atmospheric pressure to a pot temperature of 129°C. A mixture of ethanol and ethyl propionate is distilled over. Vacuum is then applied to the distillation column and the resultant product, ethyl-2-methyl-3,4-pentadienoate is distilled at a vapor temperature of 65°–69°C at a pressure of 24–33 mm Hg as fractions 5–10 of the following fractions:

| Fraction No. | Vapor Temperature | Liquid Temperature | Pressure (mm Hg) | Weight of Fraction | Reflux Rartio |
|---|---|---|---|---|---|
| 1 | 68–72°C | 127–87°C | 760 | 174.5 g | 9:1 |
| 2 | 28–42 | 86–83 | 48–50 | 19.4 | 9:1 |
| 3 | 69 | 84 | 45 | 12.6 | 9:1 |
| 4 | 65 | 79 | 34 | 20.1 | 9:1 |
| 5 | 67 | 80 | 33 | 38.9 | 4:1 |
| 6 | 67 | 82 | 33 | 32.5 | 4:1 |
| 7 | 67 | 82 | 33 | 36.8 | 4:1 |
| 8 | 67 | 83 | 33 | 37.2 | 4:1 |
| 9 | 66 | 84 | 24 | 39.8 | 4:1 |
| 10 | 65 | 94 | 24 | 36.9 | 4:1 |
| 11 | 57 | 108 | 10 | 45.5 | 4:1 |
| 12 | 39 | 172 | 2.3 | 14.5 | 4:1 |

The resulting material is confirmed by IR, NMR and mass spectral analyses to have the structure:

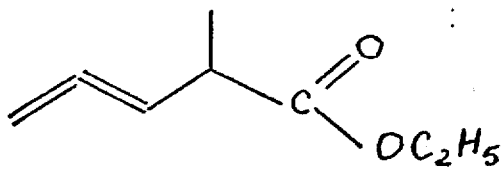

Mass spectral analysis:

Parent peak, then in order of decreasing intensity: m/e = 140(M$^+$); 67, 97, 29, 41, 125

Nuclear Magnetic Resonance Analysis:

| ppm | Interpretation | |
|---|---|---|
| 1.26 ppm (t) | $CH_3-C-O-\underset{\underset{O}{\|}}{C}-$ | 6H |
| 1.28 ppm (d) | $CH_3-\underset{\underset{O}{\|}}{C}-C-$ | 6H |
| 3.10 ppm (m) | $=C-CH-C=O$ | 1H |
| 4.12 ppm (q) | $CH_3-CH_2-O-\underset{\underset{O}{\|}}{C}-$ | 2H |
| 4.76 ppm (m) | $H_2C=C=C-$ | 2H |
| 5.40 ppm (m) | $C=C=CH$ | 1H |

The nuclear magnetic resonance spectrum is set forth in FIG. 1.

Infra Red Analysis

Peaks 850 cm$^{-1}$
1050
1175
1225
1375
1425
1730
1950
2880
2925
2975

Figure 2:
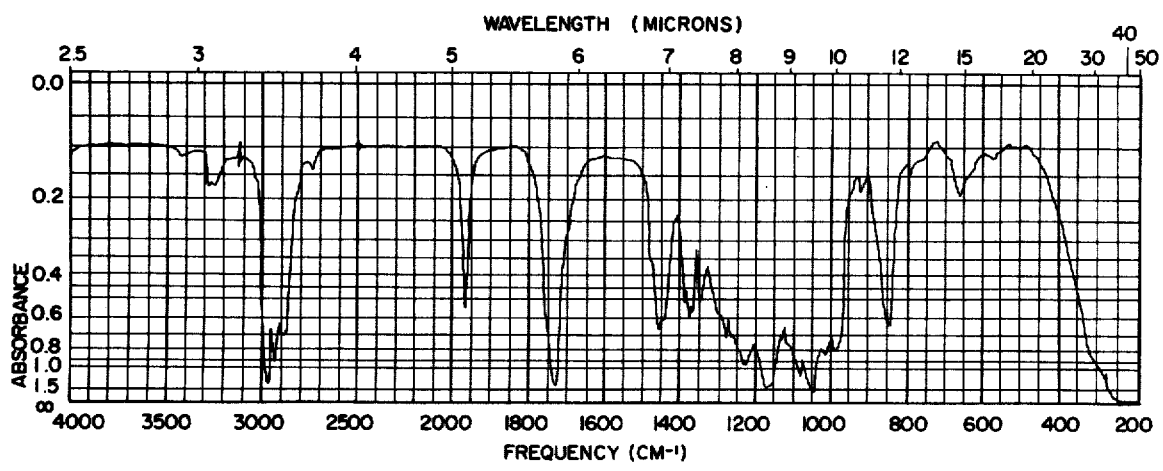

The infra-red spectrum is set forth in FIG. 2. At a concentration of 0.5 ppm, the resulting product, ethyl-2-methyl-3,4-pentadienoate has a fruity, strawberry, creamy aroma with berry, apple and pineapple notes and a sweet, fruity, strawberry flavor with woody and creamy nuances.

Note 1: Primol is a registered trademark identifying a hydrocarbon mineral oil produced by Exxon Corp. of Linden, New Jersey.
Note 2: Ionol is a registered trademark identifying the compound, 2,6-di-t-butyl-4-methyl phenol.

EXAMPLE X

HYDROGENATION OF ETHYL-2-METHYL-3,4-PENTADIENOATE USING A LINDLAR CATALYST, THEREBY PREPARING MIXTURES OF ETHYL-2-METHYL-CIS-3-PENTENOATE AND ETHYL-2-METHYL-4-PENTENOATE

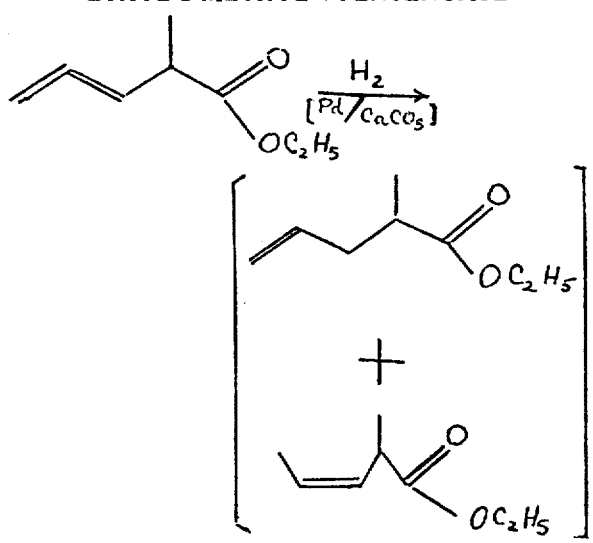

Into a 2-liter autoclave, the following ingredients are placed:

| Ingredient | Quantity |
| --- | --- |
| Ethyl-2-methyl-3,4-pentadienoate produced according to the process of Example IX | 577.8 grams |
| Palladium on calcium carbonate catalyst (Lindlar catalyst) | 1.4 grams |

The autoclave is connected by means of pressure tubing to a hydrogen-containing cylinder. The autoclave is then sealed and while adding hydrogen into the autoclave from the hydrogen-containing cylinder and maintaining the pressure within the autoclave at 60 pounds per square inch gauge, the the reaction mass is stirred. During the hydrogenation and over a 19-hour period, the reaction mass is maintained at room temperature by means of the application of cooling. At the end of the 19-hour period, the autoclave is opened; and an additional 1.4 grams of Lindlar catalyst is added. The autoclave is then closed and hydrogen is continuously added thereto while stirring the reaction mass over an additional reaction period of 10 hours. At the end of the 10-hour period, the autoclave is opened, and the reaction mass is filtered. An addition 2.8 grams of Lindlar catalyst is then added to the reaction mass which is then again placed in the autoclave with hydrogen being added thereto and pressure being maintained at 60 pounds per square inch gauge. At the end of one and three-quarter hours, GLC analysis indicates that the reaction is completed. The autoclave is then opened and the reaction mass filtered. The filtered reaction mass is then distilled on a 1 inch × 1 foot Goodloe distillation column after adding thereto 10 grams of Primol (see Note 1) and 0.1 gram of Ionol (see Note 2) yielding the following fractions.

| Fraction No. | Vapor Temp. | Liquid Temp. | Vacuum (mm Hg) Pressure) | Weight of Fraction | Reflux Ratio |
| --- | --- | --- | --- | --- | --- |
| 1 | 31–33°C | 77–86°C | 200–205 | 18.2 g | 19:1 |
| 2 | 60 | 90 | 200 | 17.0 | 19:1 |
| 3 | 61 | 93 | 200 | 11.0 | 19:1 |
| 4 | 62 | 97 | 200 | 12.6 | 19:1 |
| 5 | 62 | 100 | 200 | 13.6 | 19:1 |
| 6 | 62 | 107 | 200 | 13.5 | 19:1 |
| 7 | 62 | 111 | 200 | 14.3 | 19:1 |
| 8 | 65 | 115 | 200 | 12.5 | 19:1 |
| 9 | 81 | 119 | 200 | 13.1 | 19:1 |
| 10 | 88–110 | 116–117 | 205 | 6.6 | 19:1 |
| 11 | 112 | 117 | 205 | 6.0 | 19:1 |
| 12 | 113 | 117 | 205 | 6.2 | 19:1 |
| 13 | 113 | 118 | 205 | 7.0 | 19:1 |
| 14 | 114 | 118 | 205 | 4.5 | 19:1 |
| 15 | 114 | 118 | 205 | 17.8 | 9:1 |
| 16 | 114 | 118 | 205 | 21.5 | 9:1 |
| 17 | 114 | 118 | 205 | 23.9 | 9:1 |
| 18 | 114 | 118 | 205 | 21.2 | 9:1 |
| 19 | 115 | 120 | 205 | 24.5 | 9:1 |
| 20 | 115 | 120 | 205 | 23.2 | 9:1 |
| 21 | 115 | 120 | 205 | 10.0 | 9:1 |
| 22 | 114–115 | 119–120 | 200–205 | 20.8 | 9:1 |
| 23 | 15 | 121 | 205 | 20.8 | 9:1 |
| 24 | 115 | 121 | 205 | 15.0 | 9:1 |
| 25 | 115 | 122 | 205 | 19.3 | 9:1 |
| 26 | 115 | 124 | 205 | 17.9 | 9:1 |
| 27 | 116 | 125 | 205 | 21.9 | 9:1 |
| 28 | 116 | 128 | 205 | 18.9 | 9:1 |
| 29 | 116 | 131 | 205 | 19.0 | 4:1 |
| 30 | 116 | 144 | 205 | 24.6 | 4:1 |
| 31 | 116 | 160 | 205 | 13.5 | 4:1 |
| 32 | 111 | 200 | 205 | 6.1 | 4:1 |

Fractions 12–31 are bulked.
Fractions 12, 13, 14, 21, 23 and 31 are analyzed using GLC analysis (conditions: 10 feet × ¼ inch Carbowax 20M column programmed at 120°C–150°C).

| Fraction No. | Weight of Fraction | Percentage ethyl-2-methyl-cis-3-pentenoate | Percentage ethyl-2-methyl-4-pentenoate |
|---|---|---|---|
| 12 | 6.2 g | 57.6% | 41.6% |
| 13 | 7.0 g | 59.2% | 38.9% |
| 21 | 10.0 g | 70.9% | 28.7% |
| 23 | 20.8 g | 75.6% | 24.1% |
| 31 | 13.5 g | 93.8% | 4.9% |

The GLC curve for Fraction No. 23 is set forth in FIG. 5.

Analyses a. Ethyl-2-methyl-cis-3-pentenoate
  i. Mass Spectral Analysis: Parent Peak; then in decreasing order of intensity; m/e = 142/ C9, 41, 29, 27, 39, 68.
  ii. NMR Analysis:

| ppm | Interpretation | |
|---|---|---|
| 1.18 (d) | $CH_3$ <br> $\|$ <br> $=C-C-C=O$ | |
| 1.22 (t) | $CH_3-C-O$ | 6H |
| 1.64 (d) | $=C-CH_3$ | 3H |
| 3.40 (m) | H <br> $\|$ <br> $=C-C-C=O$ | 1H |
| 4.10 (q) | $\quad\quad O$ <br> $\quad\quad \|\|$ <br> $-CH_2-O-C-$ | 2H |
| 5.20 (m) | $HC=CH$ | 2H |

Infrared Analysis:
710, 860, 960, 1020, 1045, 1090, 1140, 1175, 1240, 1325, 1370, 1395, 1450, 1650, 1730, 2880, 2900, 2940, 2980, 3020 cm$^{-1}$ (b) Ethyl-2-methyl-4-pentenoate Mass spectral analysis: Parent peak then in decreasing order of intensity, m/e = 142/69, 41, 29, 27, 39, 68.

NMR Analysis:

| ppm | Interpretation | |
|---|---|---|
| 1.12 (d) | $CH_3$ <br> $\|$ <br> $C-C$ | |
| 1.21 (t) | $CH_2-C-O$ | 6H |
| 2.60–2.06 (m) | methine and methylene protons | 3H |
| 4.10 (q) | $\quad\quad O$ <br> $\quad\quad \|\|$ <br> $CH_3-CH_2-O-C-$ | 2H |
| 5.10–4.94 | $HC=CH_2$ | 2H |
| 5.94–5.03 | $HC=CH_2$ <br> $\|$ | 1H |

Infrared Analysis:
910, 990, 1025, 1050, 1090, 1140, 1180, 1250, 1275, 1345, 1370, 1430, 1640, 1730, 2880, 2900, 2940, 2980.

Note 1: Primol is a registered trademark identifying a hydrocarbon mineral oil produced by Exxon Incorporation of Linden, New Jersey.
Note 2: Ionol is a registered trademark identifying the compound 2,6-di-tert-butyl-4-methyl-phenol.

EXAMPLE XI

PREPARATION OF ETHYL-2-METHYL-CIS-3-PENTENOATE: ETHYL-2-METHYL-4-PENTENOATE AND ETHYL-2-METHYL PENTANOATE BY HYDROGENATION OF 2-METHYL-3,4-PENTADIENOATE USING A RANEY NICKEL CATALYST

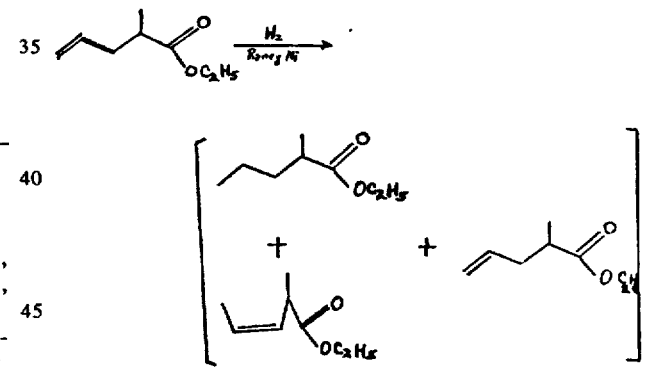

Into a 500 cc autoclave fitted by means of pressure tubing to a hydrogen-containing cylinder is added the following materials:

| Ingredient | Quantity |
|---|---|
| ethyl-2-methyl-3,4-pentadienoate prepared according to the process of Example IX | 187 grams |
| Raney nickel | 7 grams |

The autoclave is closed, and, while stirring and maintaining the temperature at 20°–30°C (using external cooling) the reaction mass is pressurized to 50 pounds per square inch gauge (psig) using hydrogen. The pressure is maintained using the hydrogen feed at 50 pounds per square inch, and the temperature is maintained at 20°–30°C over a period of 5½ hours. After 2½ hours, 1 gm mole of hydrogen was absorbed in the reaction mass; and GLC analysis shows the presence of the following materials:

| | |
|---|---|
| ethyl-2-methyl pentanoate | 2% |
| ethyl-2-methyl-4-pentenoate | 25.7% |
| ethyl-2-methyl-cis-3-pentenoate | 62.5% |
| ethyl-2-methyl-3,4-pentadienoate | 8.9% (starting material) |

The reaction is continued for another hour by repressurization using the hydrogen feed up to 50 psig. At the end of the 3½ hours, 1–19 gm moles of hydrogen is absorbed by the reaction mass, and the autoclave is opened and again GLC analysis is carried out. GLC analysis indicates the following composition in the reaction mass after 3½ hours:

| | |
|---|---|
| ethyl-2-methyl-pentanoate | 11% |
| ethyl-2-methyl-4-pentenoate | 19.7% |
| ethyl-2-methyl-cis-3-pentenoate | 68% |

The autoclave is then closed and repressurized with hydrogen to 50 psig and the reaction is continued for another 2 hours, at which time 1.5 gm moles of hydrogen (total) is absorbed by the reaction mass. At the end of the 2 hour period, the autoclave is again opened and GLC analysis indicates the following:

| | |
|---|---|
| ethyl-2-methyl pentanoate | 35% |
| ethyl-2-methyl-cis-3-pentenoate | 65% |

At the 5½ hour reaction time, it is significant to note that no ethyl-2-methyl-4-pentenoate is present in the reaction mass.

GLC analysis at 2½ hours, 3½ hours and 5½ hours are set forth in FIG. 6.

The final mixture is filtered and distilled in a 36 inches × 1½ Goodloe column after adding thereto 5.0 grams of Primol and 0.1 grams of Ionol yielding the following fractions:

| Fraction No. | Vapor Temp. | Liquid Temp. | Pressure (mm Hg) | Weight | Reflux Ratio |
|---|---|---|---|---|---|
| 1 | 50°C | 55°C | 20.0 | 7.4 | 19:1 |
| 2 | 50 | 55 | 20.0 | 8.5 | 19:1 |
| 3 | 50 | 55 | 20.0 | 8.8 | 19:1 |
| 4 | 50 | 55 | 20.0 | 14.5 | 19:1 |
| 5 | 50 | 55 | 20.0 | 15.9 | 19:1 |
| 6 | 50 | 55 | 20.0 | 11.4 | 19:1 |
| 7 | 50 | 55 | 20.0 | 12.5 | 19:1 |
| 8 | 50 | 55 | 20.0 | 11.5 | 19:1 |
| 9 | 50 | 55 | 20.0 | 11.7 | 19:1 |
| 10 | 50 | 55 | 20.0 | 11.2 | 19:1 |
| 11 | 50 | 55 | 20.0 | 22.2 | 19:1 |
| 12 | 50 | 55 | 20.0 | 11.0 | 19:1 |
| 13 | 50 | 55 | 20.0 | 11.8 | 19:1 |
| 14 | 50 | 55 | 20.0 | 12.7 | 19:1 |
| 15 | 52 | 56–57 | 20.0 | 10.0 | 19:1 |
| 16 | 52 | 57 | 20.0 | 10.9 | 19:1 |
| 17 | 52 | 57 | 20.0 | 9.5 | 19:1 |
| 18 | 52 | 57 | 20.0 | 7.0 | 19:1 |
| 19 | 52 | 57 | 20.0 | 3.7 | 19:1 |
| 20 | 53 | 58 | 20.0 | 2.6 | 19:1 |
| 21 | 53 | 58 | 20.0 | 5.8 | 19:1 |
| 22 | 53 | 59 | 20.0 | 5.5 | 19:1 |
| 23 | 53 | 63 | 20.0 | 6.0 | 19:1 |
| 24 | 53 | 95 | 20.0 | 7.5 | 19:1 |
| 25 | 53 | 140 | 20.0 | 3.8 | 19:1 |

Fraction No. 22 is analyzed using NMR, GLC and mass spectral analysis as being 95% ethyl-2-methylcis-3-pentenoate and 5% ethyol-2-methyl pentanoate. This fraction is then redistilled in order to substantially eliminate the saturated ester which counteracts the delicate strawberry taste of the unsaturated cis ester, The resulting cis ester is an excellent, fresh strawberry additive having a fruity, strawberry, pineapple aroma with rum and honey undertones suitable as a food flavor, medicinal product flavor, chewing gum flavor, perfumery adjuvant and tobacco additive. The IR, NMR and mass spectral data for the saturated and for the unsaturated esters are identical to those set forth in Examples II and III supra.

When the above process is repeated without sampling for GLC analysis at the 2½ hour and 3½ hour intervals, after 5½ hours, 1.48 gm moles of hydrogen is absorbed in the reaction mass and GLC analysis shows the following:

| | |
|---|---|
| ethyl-2-methyl pentanoate | 38% |
| ethyl-2-methyl-cis-3-pentenoate | 61.4% |

When the above procedure is repeated with sampling at 3½ hours and 4 hours, the following results are obtained:

i. 3½ hours: hydrogen uptake 1.4 gm moles percentage of ethyl-2-methyl pentanoate is 27% percentage of ethyl-2-methyl-4-pentenoate is 4% ethyl-2-methyl-cis-3-pentenoate 68% ii. 4 hours: hydrogen uptake 1.5 gm moles percentage ethyl-2-methyl pentanoate is 36% percentage ethyl-2-methyl-cis-3-pentenoate is 63.6%.

EXAMPLE XII

HYDROGENATION OF ETHYL-2-METHYL-3,4-PENTADIENOATE USING A 5% PALLADIUM ON CARBON CATALYST

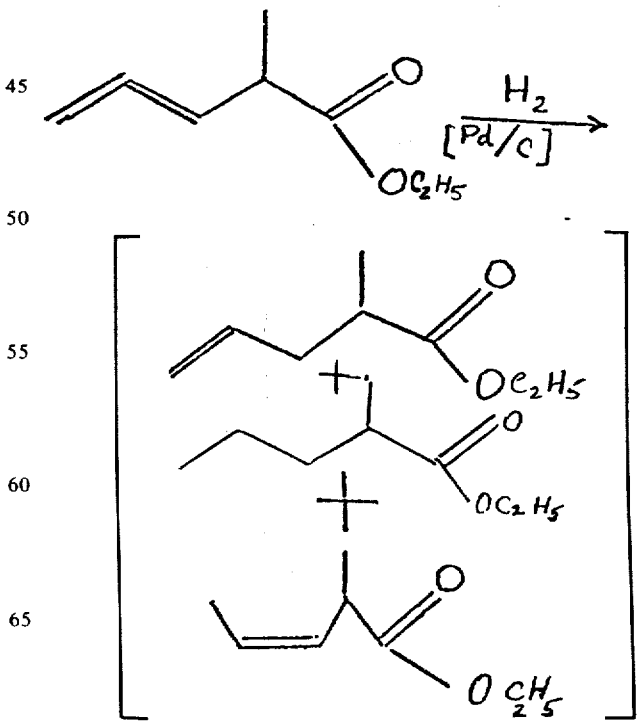

Into a 250 cc Parr Bomb, the following ingredients are placed:

| Ingredient | Amount |
| --- | --- |
| Ethyl-2-methyl-3,4-pentadienoate produced according to the process of Example IX | 25 grams |
| Palladium on carbon | 0.025 grams |

The Parr Bomb is connected by means of pressure tubing to a hydrogen-containing cylinder. The Parr Bomb is then sealed while adding hydrogen thereinto from the hydrogen-containing cylinder and maintaining pressure within the Parr Bomb at 25–50 psig. The reaction is maintained at room temperature using external cooling. After a period of 3.5 hours, the Parr Bomb is opened and the contents are filtered. GLC analysis indicates that the reaction is completed. GLC analysis (conditons: 8 feet × ½ inch carbowax column; column temperature 120°C) indicates the following components:

| Component | Weight Percent |
| --- | --- |
| Ethyl-2-methyl-cis-3-pentenoate | 65.7% |
| Ethyl-2-methyl-4-pentenoate | 14.3% |
| Ethyl-2-methyl-pentenoate | 19.9% |

The GLC spectrum is illustrated in FIG. 4.

EXAMPLE XIII

PREPARATION OF 2-METHYL-CIS-3-PENTENOIC ACID

Into a 250 ml flask equipped with stirrer, thermometer, reflux condenser and heating mantle the following materials are added:

| 50% aqueous NaOH | 60 grams |
| --- | --- |
| methanol | 50 grams |

The reaction mass heats up to 55°C and is cooled using external cooling to 20°C. Ethyl-2-cis-3-pentenoate (prepared according to Example X; bulked fractions 20–22) is then added dropwise with stirring to the reaction mass while maintaining same at a temperature of 20°C. The addition takes place over a period of 30 minutes. After addition is completed, the reaction mass is stirred for another 30 minutes. 22 grams of concentrated sulfuric acid is then added dropwise to the reaction mass with stirring. 150 ml of 5% hydrochloric acid is added bringing the reaction mixture to a pH of 4.

The reaction mass is then stirred for a period of 15 minutes and is extracted with three 150 ml portions of diethyl ether. The extracts are combined and evaporated and the concentrated material is rushed over to yield the following fractions:

| Fraction No. | Vapor Temperature | Pot Temperature | Vacuum | Weight of Fraction | % Product |
| --- | --- | --- | --- | --- | --- |
| 1 | 80 | 94 | 7.5 | 0.7 | >90% |
| 2 | 89 | 99 | 7.8 | 3.0 | >90% |
| 3 | 90 | 140 | 8.2 | 23.6 | >99% |
| 4 | 90 | 200 | 8.2 | 1.1 | >99% |

NMR, IR and Mass spectral analyses confirm the resultant material to be 2-methyl-cis-3-pentenoic acid having a purity greater than 99%.

EXAMPLE XIV

PREPARATION OF 2-METHYL-CIS-3-PENTENOIC ACID

Into a 250 ml flask equipped with stirrer, thermometer, reflux condenser and heating mantle the following materials are added:

| 50% aqueous NaOH | 60 grams |
| --- | --- |
| methanol | 50 grams |

The reaction mass heats up to 55°C and is cooled using external cooling to 20°C. Ethyl-2-cis-3-pentenoate (prepared according to Example XI; fraction 22) is then added dropwise with stirring to the reaction mass while maintaining same at a temperature of 20°C. The addition takes place over a period of 30 minutes. After addition is completed, the reaction mass is stirred for another 30 minutes. 22 grams of concentrated sulfuric acid is then added dropwise to the reaction mass with stirring. 150 ml of 5% hydrochloric acid is added bringing the reaction mixture to a pH of 4.

The reaction mass is then stirred for a period of 15 minutes and is extracted with three 150 ml portions of diethyl ether. The extracts are combined and evaporated and the concentrated material is rushed over at 90°C and 8.2mm Hg pressure.

NMR, IR and Mass spectral analyses confirm the resultant material to be 2-methyl-cis-3-pentenoic acid having a purity greater than 99%.

EXAMPLE XV

PREPARATION OF 2-METHYL-CIS-3-PENTENOIC ACID

Into a 250 ml flask equipped with stirrer, thermometer, reflux condenser and heating mantle the following materials are added:

| 50% aqueous NaOH | 60 grams |
| --- | --- |
| methanol | 50 grams |

The reaction mass heats up to 55°C and is cooled using external cooling to 20°C. Ethyl-2-cis-3-pentenoate (prepared according to Example XII) is then added dropwise with stirring to the reaction mass while maintaining same at a temperature of 20°C. The addition takes place over a period of 30 minutes. After addition is completed, the reaction mass is stirred for another 30 minutes. 22 grams of concentrated sulfuric acid is then added dropwise to the reaction mass with stirring. 150 ml of 5% hydrochloric acid is added bringing the reaction mixture to a pH of 4.

The reaction mass is then stirred for a period of 15 minutes and is extracted with three 150 ml portions of diethyl ether. The extracts are combined and evaporated and the concentrated material is rushed over at 90°C and 8.2 mm Hg pressure.

NMR, IR and Mass spectral analyses confirm the resultant material to be 2-methyl-cis-3-pentenoic acid having a purity greater than 99%.

EXAMPLE XVI

The following concentrate is prepared:

| Ingredient | Percent |
| --- | --- |
| Geraniol | 1.00 |
| Ethyl methyl phenyl glycidate | 3.33 |
| "High cis" 2-methyl-3-pentenoic acid (prepared according to the process of Example XIII or XV; or 2-methyl-cis-3-pentenoic acid prepared according to Example XIV) | 4.77 |
| Vanillin | 5.66 |
| Ethyl pelargonate | 13.06 |
| Isoamyl acetate | 14.00 |
| Ethyl butyrate | 58.18 |

EXAMPLE XVII

Another concentrate is prepared as follows:

| Ingredient | Percent |
| --- | --- |
| Naphthyl ethyl ether | 0.96 |
| Vanillin | 2.66 |
| Ethyl methyl phenyl glycidate | 2.88 |
| "High cis" 2-methyl-3-pentenoic acid (prepared according to the process of Example XIII or XV; or 2-methyl-cis-3-pentenoic acid prepared according to Example XIV) | 4.90 |
| Ethyl acetate | 9.58 |
| Isoamyl acetate | 12.25 |
| Ethyl butyrate | 26.20 |
| Isoamyl butyrate | 40.57 |

EXAMPLE XVIII

The concentrate prepared in Example XVI is dissolved in 4 volumes of propylene glycol and the mixture is added to a hard candy melt at the rate of 1.5 oz. of the concentrate solution per 100 lbs. of melt. After the finished candy has been produced, it is found to have an excellent strawberry flavor. When the candy is compared with candy made under the same conditions, but without the 2-methyl-cis-3-pentenoic acid prepared according to the processes either of Examples XIII, XIV or XV in the concentrate, it is found to have an inferior strawberry flavor.

EXAMPLE XIX

The propylene glycol solution of the concentrate as prepared in Example XVIII is added to a simple syrup at the rate of ⅛ oz. per gallon of syrup. The syrup is acidified by the addition of 1.5 oz. of 50% aqueous citric acid solution to each gallon of syrup. A carbonated beverage is prepared by admixing one oz. of the flavored, acidified syrup with 5 oz. of carbonated water. The beverage so prepared has an excellent fresh strawberry flavor, and is found to be markedly superior to a beverage prepared in the same manner but without the 2-methyl-cis-3-pentenoic acid prepared according with either of the processes of Examples XIII, XIV or XV.

EXAMPLE XX

The flavor concentrate prepared in Example XVII is admixed with gum arabic and in the proportion of 7 lbs. of concentrate to 28 lbs. of gum arabic in 65 lbs. of water, and the aqueous mixture is spray-dried. The flavor concentrate-carrier combination so obtained is then added to a gelatin dessert mix in the ratio of 1 oz. of spray-dried material to 100 lbs. of dessert mix powder. The galatin dessert produced from the mix has an excellent strawberry flavor and is markedly superior to a gelatin dessert prepared in the same manner without the 2-methylcis-3-pentenoic acid prepared according to any of the processes of Examples XIII, XIV or XV in the concentrate.

What is claimed is:

1. A process for augmenting or enhancing the berry fruit flavor of a foodstuff which comprises adding thereto as the sole ingredient for augmenting or enhancing berry fruit flavor and in an amount of from 0.01 parts per million up to about 50 parts per million by weight based on the weight of said foodstuff, a composition consisting essentially of one or more synthetically produced five carbon atom acids having the generic structure:

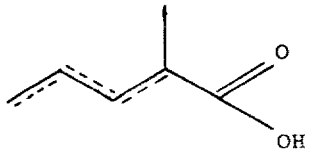

wherein one of the dashed lines represents a carbon-carbon double bond, the major constituent of said five carbon acids being 2-methyl-cis-3-pentenoic acid having the structure:

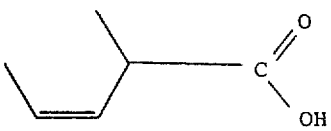

2. A flavor modifying composition useful in augmenting or enhancing the berry fruit flavor of a foodstuff consisting essentially of (i) from 0.015 up to about 10% by weight based on the total weight of said flavoring composition of one or more synthetically produced five carbon atom carboxylic acids having the generic structure:

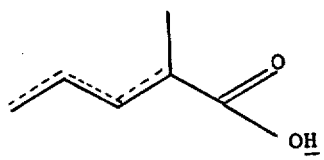

wherein one of the dashed lines is a carbon-carbon double bond, the major constituent of said five carbon carboxylic acids being 2-methylcis-3-pentenoic acid; and (ii) the remainder of said composition being at least one flavor adjuvant selected from the group consisting of geraniol, ethyl methyl phenyl glycidate, vanillin, ethyl pelargonate, isoamyl acetate, ethyl butyrate, naphthyl ethyl ether, ethyl acetate, isoamyl butyrate. 4-allyl-1,2,6-trimethoxy benzene and 4-propenyl-1,2,6-trimethoxy benzene.

3. A process for augmenting or enhancing the berry fruit flavor of a foodstuff which comprises adding thereto as the sole ingredient for augmenting or enhancing berry fruit flavor and in an amount of from 0.01 parts per million up to about 50 parts per million by weight based on the weight of said foodstuff, a composition consisting essentially of a synthetically produced approximately 3:2 cis:trans mixture of 2-methyl-3-pentenoic acid, the component of the mixture which is 2-methyl-cis-3-pentenoic acid having the structure:

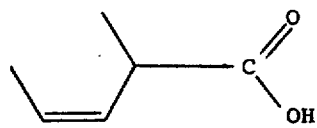

4. A flavor modifying composition useful in augmenting or enhancing the berry fruit flavor of a foodstuff consisting essentially of (i) from 0.015% up to about 10% by weight based on the total weight of said flavoring composition of a synthetically produced approximately 3:2 cis:trans isomer mixture of 2-methyl-3-pentenoic acid, the component of the mixture which is 2-methyl-cis-3-pentenoic acid having the structure:

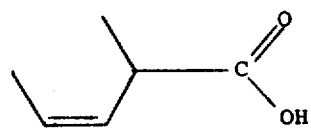

and (ii) the remainder of said composition being at least one flavor adjuvant selected from the group consisting of geraniol, ethyl methyl phenyl glycidate, vanillin, ethyl pelargonate, isoamyl acetate, ethyl butyrate, naphthyl ethyl ether, ethyl acetate, isoamyl butyrate, 4-allyl-1,2,6-trimethoxy benzene and 4-propenyl-1,2,6-trimethoxy benzene.

5. A process for augmenting or enhancing the berry fruit flavor of a foodstuff which comprises adding thereto as the sole ingredient for augmenting or enhancing berry fruit flavor and in an amount of from 0.01 parts per million up to about 50 parts per million based on the weight of said foodstuff, a synthetically produced mixture consisting of 80% of 2-methyl-cis-3-pentenoic acid having the structure:

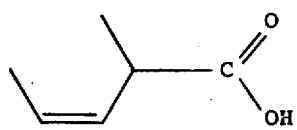

and 20% of 2-methyl-2-pentenoic acid.

6. A flavor modifying composition useful in augmenting or enhancing the berry fruit flavor of a foodstuff consisting essentially of (i) from 0.015 up to about 10% by weight based on the total weight of said flavor modifying composition of a synthetically produced mixture consisting of 80% of 2-methyl-cis-3-pentenoic acid having the structure:

and 20% of 2-methyl-2-pentenoic acid and (ii) the remainder of said flavor modifying composition being at least one food flavor adjuvant compound selected from the group consisting of geraniol, ethyl methyl phenyl glycidate, vanillin, ethyl pelargonate, isoamyl acetate, ethyl butyrate, naphthyl ethyl ether, ethyl acetate, isoamyl butyrate, 4-allyl-1,2,6-trimethoxy benzene and 4-propenyl-1,2,6-trimethoxy benzene.

7. A process for augmenting or enhancing the berry fruit flavor of a foodstuff which comprises adding thereto as the sole ingredient for augmenting or enhancing berry fruit flavor a synthetically produced composition consisting essentially of:

i. More than 60% by weight of 2-methylcis-3-pentenoic acid having the structure:

ii. Less than 40% by weight of a second acid selected from the group consisting of:
 a. 2-methyl-trans-3-pentenoic acid;
 b. 2-methyl-2-pentenoic acid;
 c. 2-methyl-4-pentenoic acid; and
 d. 2-methyl pentanoic acid said 2-methyl-cis-3-pentenoic acid being present in an amount of from 0.01 parts per million up to about 50 parts per million by weight based on the weight of foodstuff.

8. The process of claim 7 wherein said second acid is a mixture of 2-methyl-4-pentenoic acid and 2-methyl pentanoic acid.

9. The process of claim 7 wherein said second acid is 2-methyl-4-pentenoic acid.

10. The process of claim 7 wherein said second acid is 2-methyl pentanoic acid.

11. A process for augmenting or enhancing the berry fruit flavor of a foodstuff which comprises adding thereto, as the sole ingredient for augmenting or enhancing the berry fruit flavor, in an amount of from 0.01 parts per million up to about 50 parts per million by weight based on the weight of foodstuff, a synthetically produced composition consisting essentially of 2-methyl-cis-3-pentenoic acid having the structure:

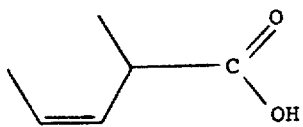

* * * * *